US012226384B2

(12) United States Patent
Zhang et al.

(10) Patent No.: US 12,226,384 B2
(45) Date of Patent: Feb. 18, 2025

(54) PERAMIVIR SOLUTION TYPE INHALANT AND PREPARATION METHOD THEREFOR

(71) Applicant: Guangzhou Nanxin Pharmaceutical Co., Ltd., Guangdong (CN)

(72) Inventors: Shixi Zhang, Guangdong (CN); Yuhuan Feng, Guangdong (CN); Dong Miao, Guangdong (CN)

(73) Assignee: Guangzhou Nanxin Pharmaceutical Co., Ltd., Guangzhou (CN)

( * ) Notice: Subject to any disclaimer, the term of this patent is extended or adjusted under 35 U.S.C. 154(b) by 610 days.

(21) Appl. No.: 17/411,044

(22) Filed: Aug. 24, 2021

(65) Prior Publication Data

US 2021/0386697 A1 Dec. 16, 2021

Related U.S. Application Data

(63) Continuation of application No. PCT/CN2019/110115, filed on Oct. 9, 2019.

(30) Foreign Application Priority Data

Feb. 25, 2019 (CN) ........................ 201910137099.2

(51) Int. Cl.

| | |
|---|---|
| ***A61K 31/196*** | (2006.01) |
| ***A61K 9/00*** | (2006.01) |
| ***A61K 9/08*** | (2006.01) |
| ***A61K 47/02*** | (2006.01) |
| ***A61K 47/26*** | (2006.01) |

(52) U.S. Cl.

CPC .......... *A61K 31/196* (2013.01); *A61K 9/0078* (2013.01); *A61K 9/08* (2013.01); *A61K 47/02* (2013.01); *A61K 47/26* (2013.01)

(58) Field of Classification Search

CPC ...... A61K 31/196; A61K 9/0078; A61K 9/08; A61K 47/02; A61K 47/26; A61P 31/16

See application file for complete search history.

(56) References Cited

FOREIGN PATENT DOCUMENTS

| | | | | | |
|---|---|---|---|---|---|
| CN | 101314579 | A | | 12/2008 | |
| CN | 101773491 | A | | 7/2010 | |
| CN | 102058522 | A | | 5/2011 | |
| CN | 102448438 | A | * | 5/2012 | ........... A61K 31/125 |
| CN | 102584637 | A | | 7/2012 | |
| CN | 102702033 | A | | 10/2012 | |
| CN | 103446051 | A | * | 12/2013 | ........... A61K 31/196 |
| WO | WO-2009143011 | A1 | * | 11/2009 | ........... A61K 31/196 |

OTHER PUBLICATIONS

Wikipedia, Hydrochloric acid, Feb. 2024.*

International search report of PCT Patent Application No. PCT/CN2019/110115 issued on Jan. 8, 2020.

Gan, Wei et al., Stability of peramivir active pharmaceutical ingredient, Drugs & Clinic, Sep. 2018, pp. 2169-2172, vol. 33, No. 9.

Zengqin Wang, Study on the decomposition of drugs during ultrasonic nebulization, International Journal of Otolaryngology—Head and Neck Surgery, 1983, p. 342, No. 6.

Lu, Hongzhou et al., Pocket Handbook of Anti-infective Agents Second Edition, Jul. 31, 2017, p. 341, Shanghai Scientific & Technical Publishers.

* cited by examiner

*Primary Examiner* — Zohreh A Fay

(57) ABSTRACT

Disclosed are a peramivir solution inhalant and a preparation method thereof, the solution inhalant includes: peramivir, an osmotic pressure regulator, a pH regulator, and water, wherein concentration of peramivir is greater than 15 mg/ml; concentration of the osmotic pressure regulator is less than 8 mg/ml; pH value of the solution inhalant ranges from 5.0 to 6.0; the peramivir solution is sterilized in a non-heating manner; the osmotic pressure regulator is selected from sodium chloride or glucose. The solution inhalant has a better stability and a good pulmonary targeting effect, which significantly improves pharmaceutical efficacy and safety.

9 Claims, No Drawings

PERAMIVIR SOLUTION TYPE INHALANT AND PREPARATION METHOD THEREFOR

CROSS-REFERENCE TO RELATED APPLICATION

The application is a Continuation Application of PCT Application No. PCT/CN2019/110115 filed on Oct. 9, 2019, which claims the priority and benefit to Chinese patent application No. 201910137099.2 filed on Feb. 25, 2019. The entirety of the above-mentioned patent applications is incorporated herein by reference and made a part of this specification.

FIELD

Embodiments of the present disclosure relate to pharmaceutical technologies, and more particularly relate to a peramivir solution inhalant and a preparation method thereof.

BACKGROUND

Peramivir with the chemical name (−)-(1S, 2S, 3R, 4R)-2-hydroxy-3-[(1S)-1-acetamido-2-ethyl]butyl-4-guanidino-cyclopenta-1-carbo xylic acid is a cyclopentane derivative neuraminidase (NA) inhibitor against influenza virus. Peramivir is a cyclopentane derivative with the following groups linked to rings: a carboxyl group and a guanidyl group which are hydrophilia, and an isopentyl group and an acetamido group which are hydrophobia, wherein the four groups of different polar act on different active site areas in the influenza virus NA structure, respectively. A strong intermolecular interaction forms between the carboxyl moiety and 3 arginine residues Arg118, Arg292 and Arg371 at the NA active site, the methyl moiety of the acetylamino group interacts with Trp 178 and Ile 222 in the NA hydrophobic pocket, while the carbonyl oxygen interacts with Arg 152; a strong intermolecular interaction forms between the guanidyl group and the Asp 151, Glu 119, Glu 227 and Trp 227 at the NA active site. For influenza B virus NA, the isoamyl moiety strongly interacts with the hydrophobic pocket consisting of Ala 246, Arg 224 and Ile 222, while for influenza A virus NA, the isopentyl moiety acts on Glu 276 hydrophobic moiety. Multiple groups on a peramivir molecule act on multiple active sites of an influenza virus NA molecule, respectively, which strongly inhibits NA activity and prevents replication and release of progeny virus particles in a host cell.

Owing to its low oral bioavailability, peramivir is mainly fabricated into a parenteral preparation such as injection. For example, CN101314579A discloses an anhydrous peramivir crystal and a pharmaceutical composition thereof, including an injection containing 200 mg anhydrous peramivir crystal, a formulation of which comprises: anhydrous peramivir crystal (200 mg), mannitol (appropriate amount), hydrochloric acid (appropriate amount), and water for injection added up to 100 ml. Further disclosed therein is a freeze-dried powder injection, a formulation of which comprises: anhydrous peramivir crystal (200 mg), mannitol (appropriate amount) and hydrochloric acid (appropriate amount), and water for injection added up to 20 ml, frozen dry.

CN102058522A discloses a piperamivir injection and a preparation method thereof. The piperamivir injection comprises: piperamivir, anhydrous solvent, cosolvent, and water for injection, wherein the weight/volume ratio (g/ml) of piperamivir to the anhydrous solvent ranges from 1:10 to 1:100, the dose ratio of the anhydrous solvent in the formulation is 20~60%(v/v), while the dose of the cosolvent is 1-20% (w/v); the anhydrous solvent refers to one or a mixture of more of ethanol, propylene glycol, glycerin, and polyethylene glycol; the cosolvent refers to one or more of glucose, sorbitol, mannitol, and cyclic hexanol. Further provided are a piperamivir injection that can be diluted with water for injection, sodium chloride or glucose infusion in any proportion while maintaining clarity, and a preparation method thereof. The disclosure provides a reasonable formulation and preparation approach that can not only improve piperamivir solubility, but also can meet injection administration requirements. With spiking of an appropriate amount of anhydrous solvent and co-solvent, piperamid solubility is increased, solution stability is maintained, solution turbidity and administration difficulty when being diluted for clinical use is avoided, dosage of anhydrous solvents is reduced as low as possible, and concentration of the bulk drug is improved. CN102702033A discloses an amorphous peramivir, a preparation method thereof, and a pharmaceutical composition thereof, wherein an injection formulation as disclosed comprises: amorphous peramivir (200 g), mannitol (appropriate amount), hydrochloric acid (appropriate amount), and water for injection added up to 100 ml.

Peramivir can dwell in a patient's respiratory tissues so as to act against influenza. Therefore, an inhalant form of peramivir, which is directly dosed to respiratory tissue lesions through non-oral routes, can mitigate potential systemic side effects. However, an inhalant can assume a plurality of dosage forms, including a dry-powder inhaler, a spray, a solution inhalant, etc. If the dry powder inhaler is applied, it would be difficult for children or aged population, or those patients with spontaneous breathing difficulties such as respiratory function deficits to inhale effective amount of medication, while the solution inhalant is more appropriate to such population. However, to prepare peramivir into a solution inhalant, there still exist various challenges.

A solution inhalant suitable for nebulization is generally required to meet some basic properties, including: 1) sterile medium; 2) low viscous liquid, low surface tension; 3) moderate pH; 4) capability of forming droplets of an average diameter less than 5 μm or 3 μm; 5) relatively stable formulation with respect to a nebulizer; 6) containing no irritating preservatives or stabilizers. Particle size and dosage form are main factors that affect the effect of an inhalation preparation, wherein particle size plays a main role. Drug delivery through inhalation potentially causes precipitation in different parts of the respiratory tract, such as the throat, trachea, bronchi, and alveoli. Generally, the smaller the particle size, the longer the particles stay suspended in the air such that the drug can be conveyed to deeper parts of the respiratory tract.

Particle size and dosage form will both affect the effect of inhaled corticosteroids. The dosage form significantly affects drug delivery to the lungs and therefore affects its efficacy. Aerosol carrier and delivery particle size are most important factors in delivering the drug to lungs. In addition, a decrease in the level of precipitation in the lungs indicates an increase in the level of oropharyngeal precipitation. Dependent on the specific dosage form used, some corticosteroids are more likely precipitated in the mouth and pharynx, potentially causing local side effects, wherein droplets precipitated on the mucus blanket covering the lung airways and nasal passages would move to the pharynx under the action of cilia. Such particles are usually large drug particles precipitated on the upper respiratory tract, which gather in the pharynx with the mucus, cells and fragments from the nasal cavity and lungs, are mixed with saliva, and swallowed into the gastrointestinal tract. Therefore, it is desirable to prepare nebulizer droplets to a smaller particle size and a narrower particle size distribution; however, such particles are difficult to prepare.

In order to achieve better nebulization, co-solvents and surfactants are usually spiked to an inhalant formulation. However, due to irritation to the respiratory tract, the co-solvents such as ethanol, polyethylene glycol and propylene glycol, which are short-chain fatty alcohols, can only be administrated with a small amount through inhalation, which are especially unsuitable for children. Besides, most surfactants are somewhat toxic. Such properties limit research and development of inhalation preparations.

A study ("Study on Drug Decomposition upon Ultrasonic Nebulization) has reported that lincomycin solution would produce sulfide after being nebulized into aerosol, causing clinical symptoms such as headache, dizziness, and nausea. Further studies have found that the stinky ultrasonic nebulized lincomycin aerosol contained dithiomethyl and hydrogen sulfide, with an unidentifiable sulfide being blended therein. In lincomycin, the side chain binding moiety containing SCH3 was prone to be decomposed by the ultrasonic energy into other sulfides; it is thus believed that potential pyrolysis could also occur to other drugs during ultrasonic nebulization. Therefore, development of peramivir solution inhalants likely faces the same problem that peramivir is potentially ultrasonic lysed.

Another document ("Study on Stability of Peramivir APIs", Gan Wei et al., Drugs & Clinic, 2018) reported that peramivir APIs (active pharmaceutical ingredients) were stable in 48 h at 100° C.; peramivir had a good stability under light irradiation for 10 days; peramivir had a good stability in alkaline and neutral environments, but was unstable in acidic conditions. With decrease of pH, the stability became deteriorated. Peramivir was very unstable in an acidic environment but was relatively stabile under alkaline and neutral conditions. Therefore, how to improve stability of peramivir solution inhalants is also a problem to be resolved.

SUMMARY

In order to overcome the above and other drawbacks in conventional technologies, embodiments of the present disclosure provide a peramivir solution inhalant, which has a good stability and thus can effectively reduce generation of related substances, and which has a smaller and more homogeneously distributed particle size and thus facilitates drug precipitation in lung tissues. Additionally, the peramivir solution inhalant according to the present disclosure has a better stability under pH 5.5. On the other hand, the peramivir solution inhalant according to the present disclosure can be target distributed in lung tissues; compared with peramivir injection, the present peramivir solution inhalant has a lung tissue drug concentration that is 1.58~5.31 times that of the intravenous administration (10 mg/kg). Furthermore, the peramivir solution inhalant according to the present disclosure can better reduce drug decomposition and chemical reaction induced during an ultrasonic process.

A technical solution of the present disclosure to solve the technical problems is provided below:

A peramivir solution inhalant, comprising: peramivir, an osmotic pressure regulator, a pH regulator, and water, wherein concentration of peramivir is greater than 15 mg/ml; concentration of the osmotic pressure regulator is less than 8 mg/ml; pH value of the solution inhalant ranges from 5.0 to 6.0; the peramivir solution is sterilized in a non-heating manner; the osmotic pressure regulator is selected from sodium chloride or glucose; after the solution inhalant is nebulized, its mass median aerodynamic diameter (MMAD) ranges from 3 μm to 4 μm, and its fine particle fraction (FPF) ranges from 60% to 80%.

In an embodiment, the concentration of peramivir is greater than 15 mg/ml but less than 25 mg/ml, preferably 20 mg/ml; the concentration of osmotic pressure regulator is less than 8 mg/ml but greater than 6 mg/ml, preferably 7 mg/ml; and the osmotic pressure regulator refers to sodium chloride.

The present disclosure preferably uses an aseptic processing, instead of a heating sterilization process.

The pH regulator refers to dilute hydrochloric acid, and more preferably, 5% dilute hydrochloric acid.

The water refers to water for injection.

In an embodiment, the peramivir solution inhalant has a pH value of 5.5, under which a good stability is offered.

The solution inhalant has a lung tissue drug concentration of greater than 7 ug/g after 1 h from aerosol inhalation, or greater than 5 ug/g after 3 h.

The fine particle dose (FPD) of the solution inhalant is greater than 10 mg, and the particle geometric standard deviation is less than 3.0.

Embodiments of the present disclosure further provide a peramivir solution inhalant, comprising: peramivir, an osmotic pressure regulator, a pH regulator, sodium dihydrogen phosphate, and water, wherein concentration of peramivir is greater than 15 mg/ml; concentration of the osmotic pressure regulator is less than 8 mg/ml; concentration of the sodium dihydrogen phosphate ranges from 0.05 to 0.2 mg/ml, pH value of the solution inhalant is 5.5; the peramivir solution is sterilized in a non-heating manner; the osmotic pressure regulator is selected from sodium chloride or glucose; after the solution inhalant is nebulized, its mass median aerodynamic diameter (MMAD) ranges from 3 μm to 4 μm, and its fine particle fraction (FPF) ranges from 60% to 80%.

The solution inhalants according to the present disclosure have a good thermostability; after being exposed to high temperature for 30 days, the content of related substances is less than 0.3%.

Embodiments of the present disclosure further provide a preparation method for a peramivir solution inhalant, comprising steps of:

mixing bulk peramivir with an adjuvant, adding 70~80° C. water up to 1000 ml, followed by agitating for dissolution and cooling, then applying dilute hydrochloric acid to regulate the pH to a range between 5.0 and 6.0, and pre-filtering the peramivir solution, followed by sterile filtering, and finally sterile filling, thereby obtaining the peramivir solution inhalant.

The present disclosure offers the following benefits:

1. The peramivir solution inhalant according to the present disclosure overcomes the peramivir injection' instability under acidic condition and effectively reduces generation of related substances; besides, the peramivir solution inhalant has a smaller and more homogeneously distributed particle size, facilitating drug precipitation in lung tissues. Furthermore, the peramivir solution inhalant has a better stability under pH 5.5.

2. The peramivir solution inhalant according to the present disclosure can be target distributed in lung tissues. Compared with peramivir injection, the present peramivir solution inhalant has a lung tissue drug concentration of 1.58~5.31 times that of the intravenous administration (10 mg/kg).

3. The peramivir solution inhalant according to the present disclosure can better reduce drug decomposition and chemical reaction caused by an ultrasonic process.

DETAILED DESCRIPTION

Hereinafter, the present disclosure will be illustrated in further detail through preferred embodiments. It should be understood that such embodiments are only for illustration purposes, rather than limiting the scope of the present disclosure. In the embodiments below, the experiment methods without noting specific conditions were generally conducted under normal conditions or the conditions advised by manufacturers.

Unless otherwise defined, all professional and scientific terms used herein take the meanings familiar to those skilled in the art. Besides, any methods and materials similar or equivalent to the disclosed contents can be applied to the methods of the present disclosure. The preferred embodiments and materials described herein are only for illustration purposes.

Example 1: Inhalant Formulations

Bulk peramivir was mixed with an adjuvant(s) in a mixing tank as per the formulations in Table 2, with 70~80° C. water for injection being added up to 1000 ml; the mixture was cooled after being agitated for dissolution; then, dilute hydrochloric acid (5% v/v) was applied to regulate the pH value to a range from 5.0 to 6.0; afterwards, the peramivir solution was pre-filtered, then sterile filtered, and finally sterile filled, thereby obtaining a peramivir solution inhalant.

The prepared solutions as per the formulations 1-9 in Table 2 were placed for 0 days, 5 days, 10 days, and 30 days under hermetic high-temperature (60° C.) and light irradiation (45001×±5001×), respectively, to investigate the conditions of related substances.

Measuring Related Substances: HPLC: Agilent 1260 Infinity USA; chromatographic column: Eclipse Plus C18 (5 μm, 4.6×250 mm, Agilent, USA); Mobile Phase: gradient elution as follows:

TABLE 1

Mobile Phase Gradient Elution

| time(min) | 0.01M potassium dihydrogen phosphate solution | methanol |
|---|---|---|
| 0 | 95 | 5 |
| 30 | 80 | 20 |
| 45 | 50 | 50 |
| 65 | 50 | 50 |

flow rate: 1 mL/min; injection volume: 20 μL;

detect wavelength: 210 nm; column temperature: room temperature.

TABLE 2

Ingredient Combinations Under Different Inhalant Formulations

| | Formulation 1 | Formulation 2 | Formulation 3 | Formulation 4 | Formulation 5 | Formulation 6 | Formulation 7 | Formulation 8 | Formulation 9 |
|---|---|---|---|---|---|---|---|---|---|
| Peramivir | 20 g | 20 g | 20 g | 20 g | 20 g | 20 g | 20 g | 20 g | 20 g |
| Vitamin C | — | 0.8 g | — | — | — | — | — | — | — |
| Citric Acid | — | — | 0.1 g | — | — | — | — | — | 0.1 g |
| sodium citrate | — | — | — | 0.4 g | — | — | — | — | — |
| disodium hydrogen phosphate | — | — | — | — | 0.1 g | — | — | — | 0.1 g |
| sodium dihydrogen phosphate | — | — | — | — | — | 0.1 g | — | 0.1 g | — |
| polyethylene glycol | — | — | — | — | — | — | 10 g | 10 g | — |
| sodium chloride | 7 g | 7 g | 7 g | 7 g | 7 g | 7 g | 7 g | 7 g | 7 g |
| 5% hydrochloric acid | Appropriate amount | Appropriate amount | Appropriate amount | Appropriate amount | Appropriate amount | Appropriate amount | Appropriate amount | Appropriate amount | Appropriate amount |
| Water for injection (bring the volume up to) | 1000 ml | 1000 ml | 1000 ml | 1000 ml | 1000 ml | 1000 ml | 1000 ml | 1000 ml | 1000 ml |

TABLE 3

| Contents (%) of Related Substances under Different Conditions | | | | | | | | | |
|---|---|---|---|---|---|---|---|---|---|
| Group # | Formulation 1 | Formulation 2 | Formulation 3 | Formulation 4 | Formulation 5 | Formulation 6 | Formulation 7 | Formulation 8 | Formulation 9 |
| 0 days | 0.11% | 0.42% | 0.10% | 0.12% | 0.13% | 0.10% | 0.08% | 0.11% | 0.13% |
| 5 days under high temperature | 0.12% | 1.31% | 0.12% | 0.14% | 0.11% | 0.13% | 0.14% | 0.21% | 0.13% |
| 10 days under high temperature | 0.13% | 1.28% | 0.12% | 0.15% | 0.16% | 0.12% | 0.32% | 0.47% | 0.18% |
| 30 days under high temperature | 0.18% | 1.41% | 0.47% | 0.77% | 0.44% | 0.20% | 1.11% | 1.21% | 0.58% |
| 5 days under light irradiation | 0.12% | 0.25% | 0.06% | 0.17% | 0.06% | 0.10% | 0.11% | 0.12% | 0.14% |
| 10 days under light irradiation | 0.13% | 0.41% | 0.25% | 0.19% | 0.13% | 0.13% | 0.13% | 0.13% | 0.16% |
| 30 days under light irradiation | 0.10% | 0.64% | 0.32% | 0.20% | 0.16% | 0.14% | 0.16% | 0.15% | 0.15% |

The experiment results showed that the inhalant solution formulated by peramivir with Vitamin C turned into a yellowish clear solution on the 5th day under light irradiation and high temperature, and related substances increased significantly on the 30th day under light irradiation and high temperature, while the other formulations were all colorless clear solutions at respective timing under high temperature and strong light irradiation conditions. Furthermore, for the inhalant solutions formulated by peramivir, sodium chloride, and at least one substance selected from sodium citrate, sodium dihydrogen phosphate, citric acid, and propylene glycol, respectively, the related substances also increased significantly after being placed under high temperature for 30 days, rendering a poor stability. However, the inhalant solution formulated by peramivir with sodium chloride and the inhalant solution formulated by peramivir with sodium chloride and sodium dihydrogen phosphate have a good stability under high temperature and light irradiation conditions.

Example 2: Experiment on Effects of Different pH to Peramivir Solubility

An excess amount of bulk peramivir was drawn and placed into a 25 ml volumetric flask, and 0.7% salt solution was applied to bring the volume to scale; the diluted solution was placed on a shaker and shaken for 24 h (25° C., 75 rpm), and then dilute hydrochloric acid (5%, V/V) was applied to regulate the pH to 4, 4.5, 5.0, and 5.5, respectively; the pH-regulated solutions were placed for another 48 h, and then filtered with a 0.45 μm filter membrane; the filtrates were diluted 250-fold with deionized water; the peramivir contents in the samples were determined by the HPLC method in peramivir standard.

TABLE 4

| Equilibrium Solubility of Peramivir in Saline Solutions of Different pH | | | | |
|---|---|---|---|---|
| pH = 4.0 | pH = 4.5 | pH = 5.0 | pH = 5.5 | pH was not regulated with 0.7% salt solution (pH = 6.86) |
| 33.93 ± 0.51 | 26.53 ± 0.14 | 22.84 ± 0.39 | 22.04 ± 0.21 | 21.48 ± 0.31 |

The experiment results showed that the equilibrium solubility of peramivir had a pH dependency; with decrease of pH, its equilibrium solubility increases. In conjunction with the preparation pH requirements (3~8) and other factors such as physiological irritation, the pH of the peramivir inhalant solution was more appropriate between 4.5 and 6.0.

Example 3: Experiment on Stability of Peramivir Inhalant Solution under Different pH Dilute hydrochloric acid (5% v/v) was applied to formulations 1 and 6 to regulate their pH values to 4.5, 5.0, 5.5, respectively; the diluted peramivir solutions and the undiluted peramivir solutions were placed under hermetic high temperature (60° C.) and light irradiation (45001x±5001x) for 0 days and 30 days, respectively, to investigate the conditions of related substances.

TABLE 5

| Contents (%) of Related Substances under Different pH Conditions | | | | | |
|---|---|---|---|---|---|
| | Group # | pH = 4.5 | pH = 5.0 | pH = 5.5 | pH = 6.86 |
| 0 days | Formulation 1 | 0.10% | 0.11% | 0.14% | 0.13% |
| | Formulation 6 | 0.13% | 0.11% | 0.12% | 0.11% |
| 30 days at high temperature | Formulation 1 | 0.86% | 0.72% | 0.29% | 0.59% |
| | Formulation 6 | 0.92% | 0.71% | 0.33% | 0.67% |
| 30 days under light irradiation | Formulation 1 | 0.36% | 0.23% | 0.23% | 0.21% |
| | Formulation 6 | 0.42% | 0.28% | 0.19% | 0.19% |

The experiment results showed that the peramivir inhalant solution was most stable under pH 5.5, and could maintain a good stability under a high temperature.

Example 4

Formulation:

| | |
|---|---|
| peramivir | 18 g |
| sodium chloride | 6.5 g |
| 5% hydrochloric acid | appropriate amount |
| water for injection | 1000 ml |

Preparation Method: mixing the bulk peramivir with the adjuvant in a mixing tank, adding 75° C. water for injection up to 1000 ml; agitating the mixture for dissolution and then cooling; applying dilute hydrochloric acid (5% v/v) to regulate the pH to 5.5, and then pre-filtering, followed by sterile filtering, and finally sterile filling, thereby obtaining the peramivir solution inhalant.

Example 5

Formulation:

| | |
|---|---|
| peramivir | 20 g |
| sodium chloride | 7 g |
| 5% hydrochloric acid | appropriate amount |
| water for injection | 1000 ml |

Preparation Method: mixing the bulk peramivir with the adjuvant in a mixing tank, adding 75° C. water for injection up to 1000 ml; agitating the mixture for dissolution and then cooling; then applying dilute hydrochloric acid (5% v/v) to regulate the pH to 5.5, and then pre-filtering, followed by sterile filtering, and finally sterile filling, thereby obtaining the peramivir solution inhalant.

Example 6

Formulation:

| | |
|---|---|
| peramivir | 15 g |
| sodium chloride | 8 g |
| 5% hydrochloric acid | appropriate amount |
| water for injection | 1000 ml |

Preparation Method: mixing the bulk peramivir with the adjuvant in a mixing tank, adding 70° C. water for injection up to 1000 ml; agitating the mixture for dissolution and then cooling; then applying dilute hydrochloric acid (5% v/v) to regulate the pH v to 5.7, and then pre-filtering, followed by sterile filtering, and finally sterile filling, thereby obtaining the peramivir solution inhalant.

Example 7

Formulation:

| | |
|---|---|
| peramivir | 20 g |
| sodium chloride | 7 g |
| sodium dihydrogen phosphate | 0.1 g |
| 5% hydrochloric acid | appropriate amount |
| water for injection | 1000 ml |

Preparation Method: mixing the bulk peramivir with the adjuvants in a mixing tank, adding 70° C. water for injection up to 1000 ml; agitating the mixture for dissolution and then cooling; then applying dilute hydrochloric acid (5% v/v) to regulate the pH to 5.5, and then pre-filtering, followed by sterile filtering, and finally sterile filling, thereby obtaining the peramivir solution inhalant.

Example 8

Formulation:

| | |
|---|---|
| peramivir | 25 g |
| glucose | 9 g |
| 5% hydrochloric acid | appropriate amount |
| water for injection | 1000 ml |

Preparation Method: mixing the bulk peramivir with the adjuvant in a mixing tank, adding 75° C. water for injection up to 1000 ml; agitating the mixture for dissolution and then cooling; then applying dilute hydrochloric acid (5% v/v) to regulate the pH to 5.5, and then pre-filtering, followed by sterile filtering, and finally sterile filling, thereby obtaining the peramivir solution inhalant.

Example 9

Formulation:

| | |
|---|---|
| peramivir | 15 g |
| sodium chloride | 8 g |
| sodium dihydrogen phosphate | 0.1 g |
| 5% hydrochloric acid | appropriate amount |
| water for injection | 1000 ml |

Preparation Method: mixing the bulk peramivir with the adjuvants in a mixing tank, adding 75° C. water for injection up to 1000 ml; agitating the mixture for dissolution and then cooling; then applying dilute hydrochloric acid (5% v/v) to regulate the pH to 5.5, and then pre-filtering, followed by sterile filtering, and finally sterile filling, thereby obtaining the peramivir solution inhalant.

Assay 1: Quality Assessment Experiment on Peramivir Aerosol Inhalation Solution

The experiment was to determine the delivery rate, total delivery amount, and fine particle dose of the Formulation 1 and Formulation 6, respectively.

Determination of Fine Particle Dose

An NGI (next-generation impactor) was placed into a refrigerator; after the temperature in the refrigerator dropped to 4° C., the experiment started. The NGI was interfaced to a low flow rate vacuum pump and a flowmeter, wherein the flow rate was tuned to 15 L/min (±5%). A plastic ampoule loaded with 2 ml peramivir aerosol inhalation solution (20 mg/ml) was drawn to shake sufficiently homogeneously; then, the ampoule bottle was squeezed to add the peramivir aerosol inhalation solution into a collection cup; the collection cup was connected to a compressor; the low flow rate vacuum pump was first started, followed by the compressor; the peramivir aerosol inhalation solution was nebulized by the compressed air generated by the compressor; 16 minutes (fully nebulized) later, the compressor was switched off, the collection cup was removed, and then the low flow rate vacuum pump was switched off. The collection cup filled with samples were detached and removed from NGI; the ampoule bottle was rinsed with deionized water/methanol (60:40) mixed solvent to recover the drug liquid to a 5 m volumetric flask; the collection cup was rinsed with the above solvent to recover the residual drug liquid into a 100 ml volumetric flask; the throat was rinsed with a diluent to collect into a 50 ml volumetric flask; the first collect layer, the second collect layer, the third collect layer, the fourth collect layer, the fifth collect layer, the sixth collect layer, the seventh collect layer, and the MOC collect layer with filter paper are rinsed with the diluent to collect into respective 50 ml volumetric flasks; parallel measurements were performed for three times. The analyte at the MOC collect layer was filtered by a 0.45 μm filter membrane, wherein the subsequent filtrate was taken as the analyte for the MOC collect layer; and the other analytes would be directly injected.

TABLE 6

Experiment Results Regarding Fine Particle Dose

| | Formulation 1 | Formulation 6 |
|---|---|---|
| Ampoule [mg] | 0.257 | 0.272 |
| Device [mg] | 27.793 | 20.931 |
| Throat [mg] | 0.389 | 0.588 |
| Stage1 [mg] | 1.123 | 1.353 |
| Stage2 [mg] | 1.496 | 2.000 |
| Stage3 [mg] | 2.531 | 3.044 |
| Stage4 [mg] | 3.308 | 3.735 |
| Stage5 [mg] | 3.419 | 3.802 |
| Stage6 [mg] | 2.355 | 2.506 |
| Stage7 [mg] | 0.919 | 1.001 |
| MOC [mg] | 0.593 | 1.024 |
| Flow Rate [L/min] | 15 | 15 |
| Doses to NGI | 1 | 1 |
| Delivery Dose [mg] | 40 | 40 |
| Total Dose Per Shot [mg] | 43.926 | 39.984 |
| Calc.Delivered Dose [mg] | 16.133 | 19.053 |
| Fine Particle Dose [mg] | 10.115 | 11.520 |
| Fine Particle Fraction [%] | 62.696 | 60.464 |
| MMAD [um] | 3.592 | 3.706 |
| GSD | 2.473 | 2.523 |
| $R^2$ | 0.999 | 0.999 |

Determination of Delivery Rate and Total Delivery Amount

A breathing simulator and a filter paper device loaded with filter paper were assembled as per instruction. A plastic ampoule loaded with 2 ml peramivir aerosol inhalation solution (20 mg/ml) was drawn to shake sufficiently homogeneously; then, the ampoule bottle was squeezed to add the peramivir aerosol inhalation solution into a collection cup; the collection cup was interfaced to a compressor; the breathing simulator was set to an adult mode (respiration frequency: 15 cycles/minutes; tidal volume: 500 ml; ratio of inhalation to exhalation: 1:1). The breathing simulator was started, wherein the duration of stage 1 was set to 1 minute; the compressor was started at the initiation of the respiration cycle and switched off at the end of the respiration cycle. The filter paper and the filter paper device were rinsed with a diluent to collect into the same 100 ml volumetric flask as the stage 1 analyte. The breathing simulator, the filter paper device loaded with filter paper, the collection cup, and the mated compressor were assembled as per instruction; the breathing simulator was started, wherein the duration of stage 2 was set to 15 minutes; the compressor was started at the initiation of the respiration cycle and switched off at the end of the respiration cycle. The filter paper and filter paper device were rinsed with the diluent to collect into the same 100 ml volumetric flask as the stage 2 analyte.

TABLE 7

Experiment Results of Delivery Rate and Total Delivery Amount

| | Formulation 1 | Formulation 6 |
|---|---|---|
| delivery rate (mg/min) | 2.23 | 2.27 |
| Total delivery amount (mg) | 8.95 | 9.64 |

The experiment results showed that for a high-concentration peramivir aerosol inhalation solution (20 mg/ml), the total delivery amount was greater than 8 mg; the FPD (fine particle dose) was greater than 10 mg; the FPF (fine particle fraction) was greater than 61%; the MMAD (mass median aerodynamic diameter) was less than 4 μm; the GSD (geometric standard deviation) was less than 3.0, thereby meeting the quality requirements with respect to aerosol inhalation solution preparations.

Assay 2: Tissue Distribution Test

Experiment Method: 15 SD male rats were drawn to be randomly assigned into 3 groups, 5 rats in each group, and peramivir sodium chloride injection (Lot No.: 3139262, Guangzhou Nanxin Pharmaceutical Co., Ltd.) was administered via intravenous injection at a dose of 10 mg/kg. 0.20 ml blood was collected from orbital venous plexus at 5 min, 1 h, and 3 h after dosing to the rats, respectively; and then the rats were lethally anesthetized to harvest the lung tissues (including trachea). After being anticoagulated by heparin sodium, the whole blood was centrifuged (1000 rpm, 5 min) to harvest the plasma; the lung tissues were rinsed and weighed; the plasma and lung tissues were placed under −20° C. until used for testing.

54 SD male rats were drawn to be randomly assigned into 9 groups, 6 rats in each group, which were administered the peramivir compound sodium chloride solution (Formulation 1) through aerosol inhalation, wherein the administration doses were low dose: 2.5 mg/kg, medium dose: 5 mg/kg, high dose: 10 mg/kg, respectively; the duration of aerosol inhalation administration was 30 min; 0.20 ml blood was collected from the orbital venous plexus at 5 min, 1 h, and 3 h after dosing to the rats, respectively; and then the rats were lethally anesthetized to harvest the lung tissues (including trachea). After being anticoagulated by heparin sodium, the whole blood was centrifuged (1000 rpm, 5 min) to harvest the plasma; the lung tissues were rinsed and weighed; the plasma and lung tissues were placed under −20° C. until used for testing.

Collect, Treatment, Analysis

Collecting Lung Tissues

The rats were lethally anesthetized at 5 min, 1 h, and 3 h after administration, respectively, with their weights weighed and recorded; then, they were exercised to remove lung tissues (including trachea); the lung tissues were rinsed with saline solution; the residual liquid was sucked dry with filter paper; the lung tissues with the residual liquid were placed in an EP tube, weighed with deduction of the weight of the EP tube the weighed weight was recorded; finally, the lung tissues were placed in a −20° C. refrigerator for storage.

Lung Tissue Pretreatment

Corresponding saline solution was spiked to the lung tissues as per the lung tissues/saline solution proportion=1 g/4 ML; the mixture was homogenized using a homogenizer; the homogenate was centrifuged at 10000 rpm for 10 min; 100 μL supernatant was drawn and placed in a 1.5 mL centrifugal tube; 400 μL 1 μg/mL internal standard oseltamivir methanol solution was precisely spiked; the mixture was vortexed for 1 min to be mixed homogeneously and then centrifuged at 12000 rpm for 10 min; 100 μL supernatant was drawn, and then 100 μL water was added and mixed sufficiently homogeneously, waiting for LC-MS/MS analysis.

Standard Protocol Lung Tissue Pretreatment

Peramivir standard solutions with concentrations of 0.5, 1, 5, 10, 50, 100, 200 μg/mL, respectively, were formulated using 1 mg/mL mother solution according to the gradient dilution method. 90 μL blank lung tissue homogenate was drawn to be precisely spiked to 10μ of the standard solution of the above concentrations, respectively, so as to prepare lung tissue standard products of concentrations of 0.05, 0.1, 0.5, 1, 5, 10, 20 μg/mL, respectively; 400 μL 1 μg/mL internal standard oseltamivir methanol solution was spiked to each lung tissue standard product; the mixed solution was vortexed for 1 min so as to be mixed homogeneously and centrifuged for 10 min at 12000 rpm; 100 μL supernatant was drawn and then spiked with 100 μL water to mix sufficiently homogeneously, waiting for LC-MS-MS analysis. The intra-day lung tissue drug concentrations were calculated according to standard protocol.

Measurement Conditions

Chromatographical Condition: Agela Venusil XBP Phenyl column (100 mm×2.1 mm, 5 μm); mobile phase A (0.1% formic acid solution, containing 2 mM ammonium acetate): B (methanol containing 0.1% formic acid)=60:40; flow rate: 0.40 mL/min; column temperature: 40° C.; injection amount: 5 μL.

Mass Spectrometric Condition: electrospray ionization source (ESI) as the ion source; detection method: positive ion detection; scanning manner: multiple-reaction monitor (MRM); ion spray voltage: 5500V; ion source temperature: 550° C.; curtain gas flow rate: 25 L/min; GS1: 50 L/min, GS2: 50 L/min, collision gas flow rate: 6 L/min; scan duration: 0.2 s; the ion conditions for quantization and qualification were shown in Table 8 and FIG. 2.

TABLE 8

Peramivir Mass Spectrographic Analysis Parameters

| | Q1 (m/z) | Q3 (m/z) | CE (V) | DP (V) | EP (V) | CXP (V) |
|---|---|---|---|---|---|---|
| Peramivir | 329.3 | 270.3 | 27 | 108 | 10.0 | 12.0 |
| Internal Standard (oseltamivir phosphate) | 313.3 | 225.2 | 14 | 67 | 10.0 | 12.0 |

Lung Tissue Drug Concentration

Studies under different administration routes and administration doses (see Table 9) showed that at 1 h and 3 h after administration of the peramivir (10 mg/kg) through intravenous injection, the lung tissue drug concentrations were all significantly lower than the respective dose groups administered through aerosol inhalation (P<0.001); at 5 min, the lung tissue drug concentrations with respect to intravenous administration were significantly lower than medium and high dose groups administered through aerosol inhalation, but there was no statistical difference from the low-dose aerosol administration (P>0.05). The lung tissue drug concentration of peramivir administrated through aerosol inhalation exhibited a dose dependency, which increased with dose. The differences in lung tissue drug concentration between the two peramivir administration routes became larger with elapse of time. Under the same dose conditions (10 mg/kg), the lung tissue concentrations of peramivir administrated through aerosol inhalation at respective timing were 2.02~41.58 times of that through intravenous administration; the lung tissue drug concentrations of low-dose administration (2.5 mg/kg) through aerosol inhalation at respective timing were 1.07~4.58 times of that through intravenous administration (10 mg/kg); the lung tissue drug concentrations of medium-dose administration through aerosol inhalation (5 mg/kg) at respective timing were 1.58~5.31 times of that through intravenous administration (10 mg/kg).

TABLE 9

Experiment Results of Lung Tissue Drug Concentrations

| Administering Route | Dose (mg/kg) | Lung Tissue Drug Concentration (Mean ± SD, μg/g) 5 min | 1 h | 3 h |
|---|---|---|---|---|
| Intravenous Injection Administration | 10 | 8.75 ± 2.63 | 2.05 ± 0.85 | 1.15 ± 1.23 |
| Aerosol inhalation Administration | 2.5 | 9.35 ± 3.08 | 7.53 ± 1.17*** | 5.19 ± 1.82*** |
| | 5 | 13.83 ± 2.99** | 7.23 ± 1.20*** | 6.11 ± 1.98*** |
| | 10 | 17.69 ± 8.88*** | 29.24 ± 7.64*** | 13.34 ± 3.27*** |
| Nebulization/ Intravenous | 2.5 | 1.07 | 3.68 | 4.50 |
| | 5 | 1.58 | 3.53 | 5.31 |
| | 10 | 2.02 | 14.29 | 11.58 |

Assay 3

Ultrasonic Nebulization Stability Experiment

The inhalant solutions as per formulation 1 and formulation 6 in Example 1 were placed in ultrasonic nebulizers (2500 KHz) for ultrasonic nebulization, respectively, to determine contents of related substance at 0 min, 20 min, 40 min, 60 min, and 90 min, respectively. The experiment results were shown in Table 10

TABLE 10

Results of Ultrasonic Nebulization Stability

| Group # | 0 min | 20 min | 40 min | 60 min | 90 min |
|---|---|---|---|---|---|
| Formulation 1 | 0.11% | 0.14% | 0.17% | 0.52% | 1.01% |
| Formulation 6 | 0.10% | 0.16% | 0.19% | 0.23% | 0.39% |

The experiment results showed that the peramivir sodium chloride solution inhalant as per formulation 1 could maintain a good stability within 40 minutes of ultrasonic nebulization at 2500 KHz; however, if the ultrasonic nebulization lasted 1 hour or more, the contents of related substances started increasing significantly, a possible cause for which was that the ultrasonic induced decomposition and further chemical reaction to the pharmaceutical ingredients; however, after sodium dihydrogen phosphate was spiked to the formulation, the related substances did not increase much within 90 minutes of ultrasonic nebulization, which significantly improved the ultrasonic stability of the drug.

What have been described above are only preferred embodiments of the present disclosure, which are not intended for limiting the substantive technical scope of the present disclosure; instead, the substantive technical scope of the present disclosure is generally limited in the appending claims. Any technical entity or method implemented by any other person, if completely identical to the scope of the appending claims, is regarded as equivalent modification, which should fall within the protection scope of the claims.

What is claimed is:

1. A peramivir solution inhalant, comprising: peramivir, an osmotic pressure regulator, a pH regulator, and water, wherein concentration of peramivir is greater than 15 mg/ml; concentration of the osmotic pressure regulator is less than 8 mg/ml; pH value of the solution inhalant ranges from 5.0 to 6.0; the peramivir solution is sterilized in a non-heating manner; the osmotic pressure regulator is selected from sodium chloride or glucose; after the solution inhalant is nebulized, its mass median aerodynamic diameter (MMAD) ranges from 3 μm to 4 μm, and its fine particle fraction (FPF) ranges from 60% to 80%.

2. The peramivir solution inhalant according to claim 1, wherein the concentration of peramivir is greater than 15 mg/ml but less than 25 mg/ml, 20 mg/ml; the concentration of the osmotic pressure regulator is less than 8 mg/ml but greater than 6 mg/ml, 7 mg/ml; and the osmotic pressure regulator refers to sodium chloride.

3. The peramivir solution inhalant according to claim 1, wherein the pH regulator refers to dilute hydrochloric acid.

4. The peramivir solution inhalant according to claim 1, wherein the pH value is 5.5.

5. The peramivir solution inhalant according to claim 1, wherein the solution inhalant has a lung tissue drug concentration of greater than 7 ug/g after 1 h from aerosol inhalation, or greater than 5 ug/g after 3 h.

6. The peramivir solution inhalant according to claim 1, wherein the fine particle dose (FPD) of the solution inhalant is greater than 10 mg, and the particle geometric standard deviation is less than 3.0.

7. A peramivir solution inhalant, comprising: peramivir, an osmotic pressure regulator, a pH regulator, sodium dihydrogen phosphate, and water, wherein concentration of peramivir is greater than 15 mg/ml; concentration of the osmotic pressure regulator is less than 8 mg/ml; concentration of the sodium dihydrogen phosphate ranges from 0.05 to 0.2 mg/ml, pH value of the solution inhalant is 5.5; the peramivir solution is sterilized in a non-heating manner; the osmotic pressure regulator is selected from sodium chloride or glucose; after the solution inhalant is nebulized, its mass median aerodynamic diameter (MMAD) ranges from 3 μm to 4 μm, and its fine particle fraction (FPF) ranges from 60% to 80%.

8. The peramivir solution inhalant according to claim 7, wherein after the solution inhalant is exposed to high temperature for 30 days, the content of related substances is less than 0.3%.

9. The peramivir solution inhalant according to claim 8, wherein the peramivir solution inhalant is prepared by a method comprising the steps of:

mixing bulk peramivir with an adjuvant, adding 70~80° C. water up to 1000 ml, followed by agitating for dissolution and cooling, then applying dilute hydrochloric acid to regulate the pH to a range between 5.0 and 6.0, and pre-filtering the peramivir solution, followed by sterile filtering, and finally sterile filling, thereby obtaining the peramivir solution inhalant.

* * * * *